United States Patent [19]

Forrest

[11] Patent Number: 4,963,345

[45] Date of Patent: Oct. 16, 1990

[54] INJECTABLE LOCAL ANESTHETIC ANTIDOTE

[76] Inventor: Kim K. Forrest, 2194 Riverside Dr., West Columbia, Tex. 77486

[21] Appl. No.: 220,160

[22] Filed: Jul. 18, 1988

[51] Int. Cl.[5] .............................................. A61K 27/00
[52] U.S. Cl. ..................................... 424/10; 514/922
[58] Field of Search ........................... 424/10; 514/922

[56] References Cited

U.S. PATENT DOCUMENTS 2,268,915  5/1939  Wastl et al. ........................... 514/578
2,919,228  12/1959  Luduena ................................ 514/47

OTHER PUBLICATIONS

*Facts and Comparisons*, p. 700, (Feb. 1988 Update).
*Dorlands Illustrated Medical Dictionary;* 25th Ed. (1974), p. 1200.

*Principles of Medicinal Chemistry,* 2nd Ed. (1981), pp. 416-417.

*Primary Examiner*—Stanley J. Friedman
*Attorney, Agent, or Firm*—Gunn, Lee & Miller

[57] ABSTRACT

An injectable antidote for local anesthetic is disclosed. In the preferred and illustrated embodiment, it is a liquid injectable having a relatively low pH typically in the range of about 2.0 to as high as about 5.5, the preferred being about 3.5. It incorporates a biologically acceptable buffering system as for example lactic acid and a suitable salt thereof such as potassium or sodium. The system also preferably includes calcium, one form being calcium lactate. A target pH is about 3.5 for this system. In addition, a vasodilator is preferably included, and alternate additional constituents are a metabolizing agent for ester based anesthetics, and also for amide based anesthetics.

9 Claims, No Drawings

INJECTABLE LOCAL ANESTHETIC ANTIDOTE

BACKGROUND OF THE DISCLOSURE

The use of a local anesthetic is essential for rendering medical care in a great multitude of situations. Probably, the most common is the injection of a local anesthetic in or about the teeth or jaw to carry on conventional, routine or extended dental work. Another example is pediatric dental work for reasons peculiar to young children. The practice of veterinary medicine requires the use of a local anesthetic often. Several examples of problems directly relating to the local anesthetic should be noted. While the problems may seem in past circumstances to be a mere inconvenience to adults, problems nevertheless can be compounded for the reasons described.

In pediatric dentistry, there is a risk of postoperative child or infant trauma as a result of the numbness in and about the mouth. It is possible for a very young child to unintentionally chew on their tongue, lip, cheek, etc. where the feeling is slow to recover. Significant injuries can potentially occur in these circumstances. In adults who have been treated for dental work, several hours may pass before the discomfort of the local anesthetic has worn off. Until that occurs, many adults speak with a thickened tongue, perhaps have discomfort during eating, and are otherwise inconvenienced.

Many medical procedures are undertaken with the assistance of a local anesthetic such as localized minor surgery or surgery on the limbs or other extremities. The numbness may last several hours. If the minor surgery under local anesthetic involves hands or feet, a person may have difficulty in using their limbs because they do not have the required tactile response or they may otherwise walk in a very wooden fashion. If a larger area is treated, it may require several hours for the numbness to wear off so that bodily sensation is restored.

A greater problem arises in veterinary surgery. There is a tendency for animals treated with a local anesthetic to chew in the region of the surgical work, perhaps mutilating the entire surgical site. As will be understood, it is not possible to orally caution very young children or animals for the interval necessary for the local anesthetic to wear off.

On a larger scale, there is the risk of excessive local anesthetic injection which has a cumulative toxicity in the entire body. It is common for Dentists to determine the approximate body weight of the patient, note the time of the first injection, calculate the rate at which the anesthetic is metabolized by the body and meter subsequent injections to avoid approaching threshold levels of toxicity. It is possible, but somewhat rare, for people to succumb to anesthetic toxicity, even to the point of death. In the event of prolonged dental or surgical work under local anesthetic, certain precautions must be undertaken. The present injectable and the method of administration contemplate reversal of the local anesthetic effect to avoid threshold toxicity conditions and thereby avoid systemic shock, perhaps toxic poisoning even to the extent of patient death.

The present disclosure sets forth what is, in its preferred form, a liquid pharmaceutical which can be injected in the ordinary fashion and which rapidly reverses or counteracts the effect of the local anesthetic. The ordinary mode is by injection and to this end, it is preferably supplied in conventional size doses in carpules. A typical quantity for dental work is 1.8 cc carpules. It is, however, able to be administered in larger quantities and is preferably administered in the region where the local anesthetic was first applied to thereby rapidly reverse the local anesthetic rather than requiring one to wait for the local anesthetic to abate merely by the passage of time. With this in view, the local anesthetic of the present disclosure and the method of use thereof are set forth in details hereinbelow.

LOCAL ANESTHETIC MECHANISM

A local anesthetic is typically an injectable which, in a near region of the body, blocks nerve conduction in the vicinity of the injection site. The mechanism of blocking a nerve signal transmission is ordinarily a reversible process which typically requires several hours to reverse the anesthetic effect. This product can be used to reduce post operative anesthetic effect from several hours to a few minutes, thereby avoiding anesthetic complications, at least the discomfort associated with anesthetized tissue and consequential trauma or injury as a result of the deadened sensory system. A typical local anesthetic molecule includes an aromatic group which after injection, but before total dispersion, creates an injection site lipophilic barrier. The molecule typically also includes some intermediate chain to a hydrophilic group on the chain. It is further known that the molecule incorporates an ester ($-COO-$) or various amides ($-NHCO-$).

Ordinarily, the local anesthetic is injected with a suitable and acceptable pharmaceutical vehicle. After injection, it works in and around the injection site with modest diffusion to enable the anesthetic molecule to block the signals transmitted along near by nerve pathways. It has been observed that modification of the local anesthetic molecule after injection significantly impacts its efficacy. As a typical example, a common injectable is chloroprocaine which incorporates a benzene ring having a chlorine atom at a particular location on the benzene ring. It has been discovered that the removal and replacement of the chlorine atom from the ortho site on the ring converts the anesthetic to procaine which is a local anesthetic of overwhelmingly reduced sensitivity.

pH CONTROL

One important aspect of the injectable local anesthetic is the mode of nerve signal interception as a result of injection and the relationship of that mechanism to the local pH in the near vicinity. In general terms, an injected local anesthetic is a weak base having a pKa in the range of about 7.5 to about 9. This is ordinarily obtained by providing an injectable anesthetic in salt form as a result of preparation with hydrochloric acid. The salt form has improved water solubility and is more stable in an aqueous media. This assists in prolonging shelf life of the injectable prior to use. The salt in a water solution, when injected in a given region, is quickly neutralized by fluid buffers in the tissue around the injection site resulting in a portion of the cations of the injectable converting to a non ionized base. The percentage of the drug which is converted into the nonionized base depends primarily on the pKa of the local anesthetic and the prevailing pH of the tissue in the region, all as given by the Henderson-Hasselbach equation. Consider as an example the injection of lidocaine which is one typical, even common local anesthetic used in dental work. Lidocaine has a pKa of about 7.9. Assume that the tissue pH is about 7.4. Prior to injection, the lidocaine is typically ionized in the range of about 95.8% to 100%. When injected into the tissue, the extracellular fluid having a pH of about 7.4 results in disassociation of about 4.68% of the injectable. This exemplifies the fact that local tissue pH significantly impacts the anesthetic action. It is well known that only the base form of the injectable anesthetic can diffuse rapidly into the nerve, penetrating the nerve sheath and coming into contact with the signal path enclosed within the nerve sheath. Accordingly, tissue acidity retards local anesthetic action. Indeed, a significant change in tissue acidity will reverse the local anesthetic action. If the tissue has a reduced pH in the area of the anesthetic, this will limit formation of the free base from the injected anesthetic, a process known as ionic entrapment. The ionic entrapment of a local anesthetic in the extracellular space of the injection site will reduce the anesthetic effect. Indeed, if the pH is substantially lowered in the general region of the local anesthetic, this can completely block anesthetic action. The present injectable thus utilizes a water based buffered salt solution providing a reduced pH. The present injectable serves as an ion trapping source which ties up the anesthetic molecules in the extracellular fluid, away from the nerve sheath, and thereby reduces the anesthetic process. The present injectable therefore has a first component, a buffered salt solution with a reduced pH which reduces extracellular acidosis. The preferred salt is a typical metal alkali such as salts of sodium, potassium, lithium, etc., sodium and potassium being the preferred cations. For reasons to be discussed below, calcium is also highly desirable and is also a preferred form. The ideal pH range of the present injectable is approximately 2.2 to 5.5, the preferred being about 3.2.

CALCIUM CONTROL

In general terms, it is known that transmission along the nerve pathway within a sheath is accomplished in part utilizing sodium conductance. The local anesthetic retards sodium conductance and hence block transmission of the nerve signal. Calcium competes for the same phospholipid receptor required for the sodium; calcium thus enhances the local anesthetic action. The present injectable is a system which reduces the available calcium ions from the neural fluid, and it reverses the calcium concentration by increasing the external calcium concentration away from the nerve sheath. The present injectable includes a constituent which is able to increase external interstitial calcium ion concentration to block inhibition of sodium conductance along the nerve pathway which therefore assists in reversing the local anesthetic effect.

ESTER AND AMIDE CONTROL

Further assistance in reduction of the local anesthetic effect to thereby accelerate patient recovery of the sensory impulses includes a constituent which chemically binds the esters and amides in the interstitial fluid to form inert but inactive by-products. It should be kept in mind that after the local anesthetic has been injected, a portion of it remains in the vicinity of the injection site and replaces that which is slowly depleted in the blocking action occurring at the nerves. In general, this is desirable because the as yet unused anesthetic molecules can then be tied up to thereby terminate the anesthetic action. Examples of compounds which chemically bind the esters and amides and their binding mechanisms are discussed below.

Esters will be considered first because they are somewhat simpler than the amides. The ester complex in an anesthetic can be deactivated by hydrolysis and it is therefore preferentially metabolized in the body plasma by pseudocholinesterase. Typical injectable derivatives of p-aminoibenzoic acid such as procaine and tetracaine can be readily hydrolyzed by this procedure. The hydrolytic cleavage products are ultimately biotransformed in the liver for routine elimination through the kidneys. The present injectable thus preferably includes a portion of pseudocholinesterase which rapidly hydrolyzes the anesthetic ester complex, thereby removing available or surplus injection site molecules before they have opportunity to initiate the local anesthetic nerve blockage.

It is somewhat more tedious to describe the metabolism of the amides. It primarily occurs in a two step sequence. The first step involves the reaction of N-dealkylation of the tertiary amino terminus. This forms a resultant amine which is susceptible to hydrolysis by amide base activity. This intermediate amine can be treated by conjugation, hydroxylation or further dealkylation. It is desirable that the resultant products of this process have minimal pharmacologic activity; otherwise the metabolic reactants may have other aspects of system toxicity.

VESSEL CONSTRICTION CONTROL

Most local anesthetics incorporate a vasoconstrictor which decreases the blood flow in the injection site so that the local anesthetic remains in that area for a longer interval. The anesthetic molecules move rather slowly through the injection site tissue and various lipid membrane barriers. The vasoconstrictor reduces capillary flow in the injection site which allows the surplus pool of anesthetic molecules in the area to accumulate around the nerve sheath. With this surplus pool of molecules available, even a small percentage of the nonionized base molecule will cross the lipid membrane or sheath of the nerve. Recall that this is the only form of the anesthetic molecule which can diffuse rapidly through the sheath. After penetration of the lipid membrane, the base must revert to the acidic form to bind available nerve receptor sites to block the nerve impulse. The vasoconstrictor extends the duration of the excess molecule pooling and hence extends the anesthetic effect. By contrast, the present injectable includes a soluble vasodilator. This overcomes the effect of the vasoconstrictor and therefore increases blood flow in the immediate region. Increased blood flow flushes the various anesthetic molecules from the region and assists in more rapid metabolism of the system and more rapid decay of the anesthetic effect. Vasodilators useful in injectable form having a relatively low toxicity and compatible with the reduced solution having a low pH are the most desirable. A typical example of a vasodilator, and indeed the preferred form, is hydralazine HCl or 1-hydrazinophtalazine monohydrochloride. This has a relatively low toxicity and a desirable pH of about 3.4 to about 4.0 and functions very successfully as a vasodilation injectable. It is well known that vasodilators have other side effects.

In sum, the present injectable is a buffered acidic solution having a relatively low pH. The optimum pH is in the range of about 3.5. The pH range is as low as about 2.2 up to about 5.0 or perhaps 5.5. It preferably includes agents which defeat the esters and amides in the anesthetic, the preferred form being pseudocholinesterase for hydrolyzing. Optionally, the ester deactivation may be sufficient that amide deactivation is not as important and can be ignored. If, however, it is necessary to increase the speed at which the amide is metabolized, then a reagent initiating the N-dealkylation of the of the amide is preferably included, an example is hepatic amidase.

MANUFACTURE OF INJECTABLE

The method of manufacture of the present injectable contemplates the formation of the buffered acidic solution which is typically mixed at room temperature and ambient pressure. The acidic buffering agents are mixed into water to provide the solution for the addition of other constituents. Consider as one example the manufacture of the injectable of the present invention. First of all, it is preferably made in deionized water which is free of dissolved gases such as carbon dioxide. The mixing process is routinely carried out in a small clean container at room temperature and atmospheric pressure. Stirring is used to assure that the materials added to the water go into solution.

The first step is designation of a target pH range. Typically, the range of the present medication is ideally about 2.0 to 5.0. A biologically acceptable buffering system can be devised, using as an example, lactic acid which is $CH_3CHOHCOOH$. A suitable biologically compatible salt is $Ca(CH_3CHOHCOO)_2$. In this example one uses 1.0 liters of water, 9.4 grams of calcium lactate salt and 5.5 grams of lactic acid stirred and dissolved in the water to yield a pH of approximately 3.5. In this particular example, the aqueous solution would then supply the appropriate calcium ion concentration so that the injection increases the external interstitial calcium ion concentration which relates to enhanced sodium conductance along the nerve pathway to assist in reversing the local anesthetic effect. Moreover, the system would represent a buffered system having a pH in the region sufficient to block the anesthetic action, as for example, to terminate prematurely the action of a typical local anesthetic such as lidocaine.

After the foregoing has been mixed and dissolved to provide the low pH solution with calcium, the vasodilator can be added. Representative types of vasodilator were described above. It was noted in the foregoing description of the vasodilator that the pH is relatively low, typically in the range of about 3.4 to about 4.0. The addition of the vasodilator to the buffered calcium solution (lactic acid and calcium lactate) does not measurably disturb the pH and provides an injectable which impacts the local anesthetic effect in three regards, namely providing a vasodilator in the presence of an excess of calcium ions in a low pH solution. Moreover, variations in vasodilator concentration do not particularly change the pH because they have overlapping pH ranges which remain biologically acceptable. As a further enhancement, ester deactivation can be accomplished by incorporating pseudocholinesterase. Amide deactivation can be accomplished by hepatic amidase. With regard to the ester hydrolyzing agent and the vasodilator, they are added in effective amounts typically in the range of about 0.1 to 1.0 molar solutions.

Another example might be to supply the calcium in the form of a salt, such as calcium chloride and thereby define a buffering system utilizing HCl. Again, the concentration of HCl can be controlled to obtain the desired pH, as for example, in the range of 2.5 to 3.0. Representative HCl concentrations are in the range of 0.05 to about 0.8. As is well known, the foregoing is soluble in water.

While the foregoing is directed to the preferred embodiment, the scope is determined by the claims which follow.

What is claimed is:

1. An injectable for defeating local anesthetic action, the injectable comprising a pharmaceutical acceptable injectable buffered acidic solution including a vasodilator.

2. The injectable of claim 1 where the vasodilator is hydralazine HCl or 1-hydrazinophtalazine monohydrochloride.

3. The injectable of claim 2 where the vasodilator has a pH not exceeding about 5.0.

4. The injectable of claim 1 wherein the buffered acidic solution includes salts of calcium salts of potassium or sodium, and wherein the salts are nontoxic to the body.

5. The injectable of claim 1 wherein the pH is in the range of about 2.5 to 5.0.

6. The injectable of claim 1 wherein a biologically acceptable acid lowers the solution pH to 5.0 or less, and including a calcium salt of the acid in solution.

7. The injectable of claim 1 wherein the acid solution concentration is biologically acceptable for injection and the pH is in the range of about 2.0 to 5.0.

8. An injectable for defeating local anesthetic action, the injectable comprising a pharmaceutical acceptable buffered calcium salt solution including a vasodilator.

9. The injectable of claim 6 wherein the vasodilator is hydralazine HCl or 1-hydrazinophtalazine monohydrochloride.

* * * * *